United States Patent [19]

Shen

[11] Patent Number: 4,515,958
[45] Date of Patent: May 7, 1985

[54] PROCESS FOR PREPARING 1-ALKYL-5-MERCAPTOTETRAZOLES

[75] Inventor: Ming Shen, Guilford, Conn.

[73] Assignee: Olin Corporation, Cheshire, Conn.

[21] Appl. No.: 517,103

[22] Filed: Jul. 25, 1983

[51] Int. Cl.$^3$ .......................................... C07D 257/04
[52] U.S. Cl. .................................................. 548/251
[58] Field of Search ........................................ 548/251

[56] References Cited

U.S. PATENT DOCUMENTS 3,437,665  4/1969  Maggiulli et al. .................. 260/308
4,110,338  8/1978  Kamiya et al. ....................... 260/308

OTHER PUBLICATIONS

E. Lieber, C. N. Pillai and R. D. Hines, Canadian Journal of Chemistry, vol. 35, 832–842 (1959).
E. Lieber and J. Ramachandran, Canadian Journal of Chemistry, vol. 37, 101–109 (1959).
F. R. Benson, Heterocyclic Compounds vol. 8, pp. 34 & 35, R. C. Elderfield, ed. John Wiley and Son, Inc. NY, NY 1967.
R. Stolle and Fr, Henke Stark, Chemical Abstracts, vol. 24, p. 2748.

Primary Examiner—Glennon H. Hollrah
Assistant Examiner—D. P. Springer
Attorney, Agent, or Firm—William A. Simons; Thomas P. O'Day

[57] ABSTRACT

A process for making 1-alkyl-5-mercaptotetrazoles of the formula:

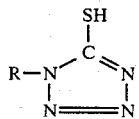

wherein R is an alkyl group having 1 to 6 carbon atoms, comprising the steps of:
(a) reacting (i) the corresponding 4-alkylthiosemicarbazide of the formula:

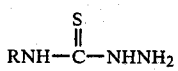

wherein R is defined above with (ii) a base of the formula:

MB wherein M is a metal cation selected from the group consisting of alkali metal cations and B is selected from the group consisting of a hydroxide or an alkoxide and with (iii) an alkyl nitrite of the formula:

Ti R$_1$ONO wherein R$_1$ is an alkyl group having 1 to 8 carbon atoms to form a reaction mixture comprising the metal salt of 1-alkyl-5-mercaptotetrazole; and
(b) contacting said reaction mixture with sufficient acid to convert at least a major portion of said metal salt of said 1-alkyl-5-mercaptotetrazole into free 1-alkyl-5-mercaptotetrazole.

11 Claims, No Drawings

PROCESS FOR PREPARING 1-ALKYL-5-MERCAPTOTETRAZOLES

BACKGROUND OF THE INVENTION

1. Field of the Invention

This invention relates to a process for making 1-alkyl-5-mercaptotetrazoles.

2. Description of the Prior Art

1-Alkyl-5-mercaptotetrazoles (also called 1-alkyltetrazole-5-thiols) are useful intermediates for making cephalosporin-type antibiotics. This class of chemical intermediates has been made by various routes. For example, these compounds have been prepared by the addition of metal azides to isothiocyanates; by the displacement of the alkylmercapto group from alkyl (N-alkyl) dithiocarbamate with metal azides; by the displacement of a halogen atom from a 5-halotetrazole with a sulfur nucleophile; and by reaction of a sulfur-protected thiosemicarbazide with nitrous acid followed by removing the protecting group from the sulfur.

While these reported syntheses have academic interest, they all suffer commercial disadvantages of either employing multi-pot reactions or starting from expensive or possibly hazardous reactants (e.g., metal azides) or have all of these problems. Thus, there is a need in the art for a simple one-pot synthesis starting from relatively inexpensive reactants. The present invention is believed to be a solution to that need.

BRIEF SUMMARY OF THE INVENTION

The present invention, therefore, is directed to a process for making 1-alkyl-5-mercaptotetrazoles of the formula (I):

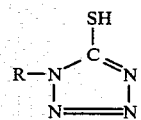
(I)

wherein R is an alkyl group having 1 to 6 carbon atoms, comprising the steps of:

(a) reacting (i) the corresponding 4-alkylthiosemicarbazide of the formula (II):

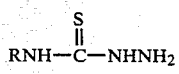
(II)

wherein R is as defined above with (ii) a base of formula (III):

MB   (III)

wherein M is a metal cation selected from the group consisting of alkali metal cations and B is selected from the group consisting of a hydroxide or an alkoxide and with (iii) an alkyl nitrite of the formula (IV):

RONO   (IV)

wherein R is an alkyl group having 1 to 8 carbon atoms to form a reaction mixture comprising the metal salt of 1-alkyl-5-mercaptotetrazole; and (b) contacting said reaction mixture with sufficient acid to convert at least a major portion (i.e., above about 50% by weight) of said metal salt of 1-alkyl-5-mercaptotetrazole into free 1-alkyl-5-mercaptotetrazole.

DETAILED DESCRIPTION

The 4-alkylthiosemicarbazide reactants of the present invention are commercially known compounds which may be made by a variety of syntheses. For example, one route for making 4-methylthiosemicarbazide involves reacting methylhydrazine and ammonium thiocyanate in the presence of water at a reaction temperature from 70°–170° C. This reaction forms the intermediate methylhydrazine thiocyanate, which immediately rearranges to form the desired product. Other processes for making this class of reactants of the present invention are disclosed in U.S. Pat. Nos. 4,237,066 (issued to Barton on Dec. 2, 1980); 4,132,736 (issued to Cramm et al on Jan. 2, 1979); and 4,173,581 (issued to Steinacher et al on Nov. 6, 1979).

The bases which may be employed for the present reaction include alkali metal hydroxides and alkali metal alkoxides. The preferred bases include potassium hydroxide and potassium alkoxides such as potassium t-butoxide. The employment of the potassium cation is preferred over a sodium cation. The term "alkoxide" as used herein includes all alkyl radicals having from 1 to 8 carbon atoms.

The alkyl nitrites which may be employed in the present reaction include those having alkyl groups with 1 to 8 carbon atoms. Generally, the most widely available alkyl nitrites are n-butylnitrite, isoamylnitrite, and 2-ethylhexylnitrite.

The preferred mole ratios of base to 4-alkylthiosemicarbazide to be employed are from about 0.9:1 to about 1.25:1. More preferably, this mole ratio should be in the range from about 0.95:1 to about 1.1:1 with the closer to about 1:1 molar ratio being the optimum.

The preferred molar ratio of the nitrosation agent to the 4-alkylthiosemicarbazide is from about 0.8:1 to about 1.5:1. More preferably, this molar ratio is from about 1.05:1 to about 1.25:1. It is desired to use a slight excess of the nitrosation agent.

The other reaction parameters are also not critical to the present process. Any suitable reaction temperature, pressure, and time may be employed. It is preferred to use a reaction temperature in the range of from about 20° C. to about 90° C. More preferably, it is desired that the reaction temperature be in the range from about 40° C. to about 85° C. It is preferred to employ atmospheric pressure but sub- or super-atmospheric reactors could be employed if desired.

Any suitable mode of adding the three reactants into the reactor may be employed. It is preferred to first combine the 4-alkylthiosemicarbazide with the base to form a metal salt. Then the nitrosation agent is added to this reaction mixture containing the metal salt thereby forming a metal salt of the desired 1-alkyl-5-mercaptotetrazole. This two-step addition appears to facilitate the reaction and produces slightly higher yields than combining all the reactants at once. The term "metal salt" as used herein includes any alkali metal salts of the 4-alkylthiosemicarbazide and 1-alkyl-5-mercaptotetrazole that may be formed by the present reaction.

The acid contacting step is normally carried out by merely adding a sufficient amount of acid to the reaction mixture containing the metal salt of 1-alkyl-5-mercaptotetrazole. The acid will convert this metal salt into the free desired product. Preferably, the amount of acid contacted with the reaction mixture is sufficient to convert substantially all (i.e., above about 90% by weight) of the metal salt to the free desired product. This may be accomplished by preferably adding at least 0.9 moles acid per mole of metal salt. It is preferred to use mineral acids such as hydrochloric acid, sulfuric acid, phosphoric acid and the like. Most preferably, hydrochloric acid is employed. Besides addition of acid, the contacting may be carried out by other conventional means such as passing the reaction mixture through an ionic exchange column containing acidic groups which will neutralize the metal salt.

After the free 1-alkyl-5-mercaptotetrazole has been formed in the reaction mixture by the acid contacting step, it may be recovered therefrom by any suitable means. Preferred recovery techniques may include solvent extraction and filtration steps and the like. Recrystallization techniques may be also employed to obtain a highly pure product.

The process of this invention has the advantage that it can be employed in a one pot system and that it utilizes relatively inexpensive starting materials.

The following examples further illustrate the present invention. All parts and percentages are by weight unless otherwise expressly indicated.

EXAMPLE 1

A solution/slurry of 4-methylthiosemicarbazide [5 grams (0.048 moles)] in ethanol (50 ml) was stirred rapidly while potassium t-butoxide [5.4 grams (0.048 moles)] was added. An exothermic reaction was observed. After this addition, this mixture was stirred for 30 minutes at room temperature. To this mixture, n-butylnitrite [5.2 grams (0.051 moles)] was then added dropwise to the light brown solution while stirring. The slow addition of the n-butylnitrite was employed so that the reaction temperature would not rise above 60° C. After that addition, the reaction mixture was heated with stirring at 80° C. under a nitrogen blanket for 1 hour and then cooled with stirring to room temperature.

The reaction mixture was then acidified with a 10% by weight aqueous HCl solution [16 ml (0.044 moles HCl)] while placed in an ice-water cooling bath (0° C.). After this acid addition, the insoluble by-products were removed by filtration. The filtrate was then freed of the ethanol solvent under vacuum formed by a water aspirator (20 mm Hg). Then, water (10 ml) and ethylacetate (30 ml) were both added to the resulting residue. The water layer was separated from the organic layer. The separated water layer was then extracted three times with ethylacetate (3×30 ml) to obtain more product from the water. The ethylacetate layer and extractions were combined and dried by addition of anhydrous magnesium sulfate. After removal of the drying agent by filtration, the ethylacetate solvent was removed under reduced pressure formed by a water aspirator. The resulting residue was vacuum dried to give a light yellow solid [3.3 grams (0.028 moles)] in 59% yield based on 4-methylthiosemicarbazide. The product was identified as 1-methyl-5-mercaptotetrazole by NMR and IR analyses and by melting point [123°–124° C. (from CHCl$_3$) vs. reported 123.5°–124° C.]. The elemental analysis was as follows:

Elemental analysis calculated for C$_2$H$_4$N$_4$S: C, 20.38; H, 3.47; S, 27.56. Found: C, 20.36; H, 3.28; S, 27.21.

EXAMPLE 2

An ethanolic solution of potassium hydroxide prepared from 85.6% potassium hydroxide pellets [9 grams (0.14 moles)] and ethanol (150 ml) was stirred rapidly while 4-methylthiosemicarbazide [15 grams (0.14 moles)] was added in a slow stream to the solution. An endothermic addition was observed. After this addition, the reaction was heated to 65° C. and then cooled to room temperature. N-butylnitrite [15.5 grams (0.15 moles)] was added dropwise while stirring to the solution. The slow addition of the n-butylnitrite was employed to control the reaction temperature from rising above 60° C. After addition, the brown reaction mixture was heated with stirring at 80° C. under a nitrogen blanket for 1 hour and cooled with stirring to room temperature. The reaction mixture was then acidified with 10% by weight aqueous HCl solution [45 ml (0.12 moles)] in an ice-water cooling bath (0° C.). After this acid addition, the insoluble by-products were removed by filtration. The filtrate was then freed of the ethanol solvent under vacuum formed by a water aspirator (20 mm Hg). Then, water (30 ml) and ethylacetate (90 ml) were both added to the resulting residue. The two phase solution was filtered, and the water layer was separated from the organic layer. The separated water layer was extracted three times with ethylacetate (3×90 ml). The ethylacetate layer and extractions were combined and dried by addition of anhydrous magnesium sulfate. After removal of the drying agent by filtration, the ethylacetate solvent was removed under reduced pressure formed by a water aspirator (20 mm Hg). The resulting residue was vacuum dried to give a yellow solid of the 1-methyl-5-mercaptotetrazole [10.4 grams (0.090 moles)] in 65% yield based on 4-methylthiosemicarbazide. The product was identified by NMR and IR analyses.

EXAMPLE 3

An ethanolic solution of potassium hydroxide prepared from 85.6% potassium hydroxide pellets [32 grams (0.49 moles)] and ethanol (250 ml) was stirred rapidly while 4-methylthiosemicarbazide [50 grams (0.48 moles)] was added in a slow stream to the solution. An endothermic addition was observed. After this addition, the reaction was heated to 60° C. and then cooled to room temperature. N-butylnitrite [64 grams (0.62 moles)] was added dropwise while stirring to the solution. The slow addition employed was to avoid the rise of the reaction temperature above 60° C. After addition, the brown solution was heated with stirring at 81° C. under a nitrogen blanket for 1 hour and cooled with stirring to room temperature. The ethanol solvent was removed under reduced pressure formed by a water aspirator. Then, water (60 ml) was added to dissolve the resulting residue of the potassium salt of 1-methyl-5-mercaptotetrozole. The aqueous solution thus obtained was extracted three times with toluene (3×20 ml) to remove any organic impurity and then acidified with concentrated HCl (40 ml) in an ice-water cooling bath (0° C.). After this acid addition, toluene (500 ml) was added to it, and the water was azeotroped off using a Dean-Stark trap. The hot anhydrous toluene solution was filtered to remove the insoluble potassium chloride salt in toluene, and then freed of the toluene solvent under reduced pressure formed by a water aspirator. The resulting residue was taken up in hot ethanol (60 ml) and filtered to remove the insolubles. The filtered ethanolic solution was freed of the ethanol solvent to give a yellow solid. The yellow solid was vacuum dried to give the 1-methyl-5-mercaptotetrazole [35.1 grams (0.30 moles)] in 62.5% yield based on 4-methylthiosemicarbazide. The product was identified by NMR and IR analyses.

EXAMPLE 4

The procedure of Example 1 was followed except isoamylnitrite [6 grams (0.050 moles)] was employed as the nitrosation agent. The recovery steps for obtaining the 1-methyl-5-mercaptotetrazole were the same. The yield based on the 4-methylthiosemicarbazide was 67%. Again, the product was identified by NMR and IR analyses.

EXAMPLE 5

The procedure of Example 1 was followed except 85.6% potassium hydroxide [5 grams (0.048 moles)] was employed as the base instead of potassium t-butoxide and isoamylnitrite [6 grams (0.050 moles)] was employed as the nitrosation agent instead of n-butylnitrite. The recovery steps for obtaining the 1-methyl-5-mercaptotetrazole were the same. The yield based on the 4-methylthiosemicarbazide was 73%. Again, the product was identified by NMR and IR analyses.

What is claimed is:

1. A process for making 1-alkyl-5-mercaptotetrazoles of the formula:

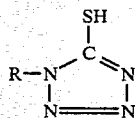

wherein R is an alkyl group having 1 to 6 carbon atoms, comprising the steps of:
(a) reacting (i) the corresponding 4-alkylthiosemicarbazide of the formula:

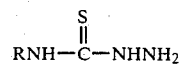

wherein R is defined above with (ii) a base of the formula:

MB wherein M is a metal cation selected from the group consisting of alkali metal cations and, B is selected from the group consisting of a hydroxide or an alkoxide and with (iii) an alkyl nitrite of the formula:

R₁ONO wherein $R_1$ is an alkyl group having 1 to 8 carbon atoms to form a reaction mixture comprising the metal salt of 1-alkyl-5-mercaptotetrazole; and
(b) contacting said reaction mixture with sufficient acid to convert at least a major portion of said metal salt of said 1-alkyl-5-mercaptotetrazole into free 1-alkyl-5-mercaptotetrazole.
2. The process of claim 1 wherein R is methyl.
3. The process of claim 1 wherein said base is potassium hydroxide.
4. The process of claim 1 wherein said base is potassium t-butoxide.
5. The process of claim 1 wherein said nitrosation agent is isoamylnitrite.
6. The process of claim 1 wherein said nitrosation agent is n-butylnitrite.
7. The process of claim 1 wherein said acid is a mineral acid.
8. The process of claim 1 wherein the molar ratio of said base to said 4-alkylthiosemicarbazide is from about 0.9:1 to about 1.25:1.
9. The process of claim 1 wherein the molar ratio of said nitrosation agent to said 4-alkylthiosemicarbazide is about 0.8 to about 1.5:1.
10. The process of claim 1 wherein said reaction temperature is from about 20° C. to about 90° C.
11. The process of claim 1 wherein sufficient acid is added to said reaction mixture to convert substantially all of the metal salt of said 1-alkyl-5-mercaptotetrazole into free 1-alkyl-5-mercaptotetrazole.

* * * * *